United States Patent [19]

Dawson et al.

[11] 4,169,012

[45] Sep. 25, 1979

[54] STABILIZED PEROXIDASE REAGENT FOR ENZYME IMMUNOASSAY

[75] Inventors: Edward C. Dawson, Berghem; Jan D. H. Homan; Bauke K. Van Weemen, both of Oss, all of Netherlands

[73] Assignee: Akzona Incorporated, Asheville, N.C.

[21] Appl. No.: 831,817

[22] Filed: Sep. 9, 1977

[30] Foreign Application Priority Data

Sep. 24, 1976 [NL] Netherlands ..................... 7610608

[51] Int. Cl.$^2$ ..................... C07G 7/00; C07G 7/02; G01N 31/14
[52] U.S. Cl. ..................................... 435/7; 435/188
[58] Field of Search ................ 195/63, 99, 103.5 R, 195/103.5 C, 103.5 A; 424/12

[56] References Cited

U.S. PATENT DOCUMENTS

| | | | |
|---|---|---|---|
| Re. 29,169 | 4/1977 | Schuurs et al. | 195/103.5 A |
| 2,990,338 | 6/1961 | Gibson | 195/103.5 C |
| 3,367,842 | 2/1968 | Rupe | 195/103.5 C |
| 3,912,593 | 10/1975 | Barker et al. | 195/63 |

*Primary Examiner*—David M. Naff
*Attorney, Agent, or Firm*—Robert H. Falk; Charles A. Wendel; Francis W. Young

[57] ABSTRACT

New and useful stable peroxidase compositions are disclosed which are particularly useful as reagents in enzyme immunoassay (EIA) tests. The novel peroxidase compositions contain polyvalent ions of groups 3 and 4 of the Periodic Table. These novel compositions are stable even in low concentrations, and are relatively invulnerable to freeze-drying. Preferably, the polyvalent ions selected are those of Al, Zn, Mg, Fe, and Cu.

6 Claims, No Drawings

STABILIZED PEROXIDASE REAGENT FOR ENZYME IMMUNOASSAY

BACKGROUND TO THE INVENTION

1. Field of the Invention

The invention relates to a method for the stabilization of compositions containing peroxidase.

It is known that peroxidases, whether or not coupled to another component, are not very stable, particularly in low concentrations, and that their keeping qualitites are therefore poor.

It has furthermore been shown that compositions containing peroxidases are very sensitive and vulnerable to freeze-drying.

Peroxidases are enzymes which catalyse the oxidation of certain compounds, during which oxidation a peroxide, and in particular hydrogen peroxide, functions as donor. They may be obtained from plants, for example horse radish peroxidase, from vertebrate animals, for example tryptophan pyrrolase, and from micro-organisms, such as cytochrome c peroxidase from Pseudomonas.

Peroxidases are used for very diverse purposes, including their use as reagents in diagnostic determinations, e.g. as a reagent in the glucose oxidase method for determining glucose, and their importance has increased even more since the development of the so-called enzyme immunotest, an immunological method of estimation for the demonstration of haptens, antigens and antibodies in which an immunological component, for example an antigen, coupled to an enzyme is used as a reagent.

2. Description of the Prior Art

After the reaction between the component to be estimated and the added component(s), the enzyme activity of the final reaction mixture, or a certain fraction thereof, is measured, and this enzyme activity is a measure of the quantity of the component to be estimated. A larger number of variations on this immunological test method, and use of different techniques, are known. A possible way of performing the test for the demonstration of an antigen, for example HCG for the demonstration of pregnancy, consists of incubating a urine sample with a certain quantity of a coupling-product of HCG and an enzyme, and a certain quantity of an antibody against HCG, which has been rendered insoluble or may afterwards be rendered insoluble. A competitive reaction takes place between antibody and the HCG to be demonstrated on the one hand and between antibody and HCG coupled to enzyme on the other hand. After the immunochemical reaction has ceased, the enzyme activity in the solid or liquid phase of the reaction product finally obtained is measured, the said activity being a measure of the HCG to be estimated.

Use is preferably made of a peroxidase as enzyme-label in this enzyme immunotest, one of the reasons being that the activity of such an enzyme may be readily determined by colourimetric means, which means that the estimation in qualitative determinations may occur visually.

Test combinations which are marketed for the performance of enzyme immunotests therefore contain as an essential constituent a certain amount of an immunological component coupled to a peroxidase, whereby the reagents are preferably provided in a lyophilized state. As noted above, the major disadvantage of peroxidases is however that their qualities in low concentrations, either in dissolved or suspended state, are not kept over any substantial period of time. The peroxidase activity may also decrease during, or as a result of, freeze-drying. For these reasons, the attractiveness of the use of peroxidases is nullified.

SUMMARY OF THE INVENTION

It has surprisingly now been found that the stability of compositions containing peroxidase, whether or not lyophilized, can be substantially increased by the addition of polyvalent metal ions to the composition.

DESCRIPTION OF THE PREFERRED EMBODIMENTS

All polyvalent metal ions may be used but suitable polyvalent ions are particularly those ions of groups 3 and 4 of the Periodic Table, to wit Mg, Ca, Se, Ti, V, Cr, Mn, Fe, Co, Ni, Cu, Zn, Ga, and Al. Preferable polyvalent ions include Al, Zn, Mg, Fe, and Cu, and most preferably Fe ions are used, particularly ferrous ions, since these exhibit in general a greater stabilizing effect than other metal ions.

The metal ions are usually added to the composition in the form of the appropriate metal salts, such as sulphates, phosphates, halides or nitrates.

The minimum amount of metal derivatives necessary for obtaining a stabilizing effect is 0.0001 M. The maximum quantity is not subject to strict limits, but optimal stability is generally achieved by the addition of 0.05 M, so that further addition is acceptable but unnecessary and extravagent. The quantity of peroxidase present in the aqueous medium to which the above-noted amount of metal derivative is added is between 1 nanogram and 25 micrograms per milliliter, and is generally between 10 nanograms and 10 micrograms.

It is recommendable that a suitable sequestering agent also be added to the composition, in order to prevent interference of the metal ions with the immunological estimation which will later be performed. Surprisingly, addition of a sequestering agent has no detrimental effect on the stabilizing ability of the metal ions. As examples of suitable sequestering agents are mentioned: ethylene diamine tetra-acetic acid (EDTA), citric acid, tartaric acid, glucuronic acid, saccharic acid, and suitable salts of these acids.

In addition to the above-noted components, other constituents may also be added to the composition, such as a buffer, sugars, for example sucrose, sorbitol or mannitol, a polyethylene glycol and/or proteins, such as albumin.

The aqueous peroxidase-containing compositions, to which a stabilizing amount of metal ions and optionally other components have been added, may be marketed as such, though they are usually first lyophilized.

Freeze-drying of the aqueous peroxidase-containing compositions takes place in the usual way by freezing at $-40°$ C. to $-50°$ C. and sublimation of the ice under reduced pressure.

Prior to the sublimation, the aqueous composition may also be brought into the form of granules by spraying into the air, or by allowing droplets of the aqueous composition to fall into a liquid which is not miscible with water and which is, either throughout or in part, at a temperature below the freezing point of the aqueous composition. The advantage of this latter possibility is that freeze-dried granules are obtained, containing previously determined and accurately measured quantities of reagents.

The following table indicates the result of the stabilizing influence of a number of metal ions, added to a peroxidase preparation; the numbers represent the time in weeks after which more than 80% of the original enzyme activity can still be detected.

| Metal ion | concentration | Temperature, °C. | | |
|---|---|---|---|---|
| | | 4 | 25 | 37 |
| Control | — | 8 | 2 | 1 |
| Al$_2$(SO$_4$)$_3$ | 0.01 | 16 | 16 | 10 |
| MgSO$_4$ | 0.01 | 16 | 2 | 1 |
| ZnCl$_2$ | 0.01 | 16 | 2 | 1 |
| FeSO$_4$ | 0.01 | 20 | 20 | 20 |

The following examples give a number of compositions which serve to further illustrate the invention.

EXAMPLE I

A preparation containing horse radish peroxidase (HRP-RZ 0.6) and albumin (BSA) in a ratio of 1:10 was dissolved in the following buffers:

(a) 0.02 M phosphate buffer, pH 6.0, 0.1% lactalbumin, 2.5% mannitol and $10^{-4}$ M FeSO$_4$.

(b) As (a), but omitting FeSO$_4$.

The content of HRP in both solutions was 12 ng/ml. The solutions were freeze-dried in vials.

The peroxidase activities of the products were determined immediately after freeze-drying; the enzyme activity in product (a) was unchanged, while product (b) possessed only 38% of the original enzyme activity.

EXAMPLE II

Horse radish peroxidase (RZ 0.6) was dissolved (8 μg/ml) in the following buffers:

(a) 0.01 M HEPES pH 8.0, 2% sucrose, 6% mannitol and 0.01 M FeSO$_4$.

(b) As (a) but omitting FeSO$_4$.

In both cases, droplets of about 50 μl were collected in liquid nitrogen, after which they were freeze-dried and kept at room temperature.

After 52 weeks, 80% of the original peoxidase activity was still present in product (a), while product (b) possessed only 17% of the original activity.

EXAMPLE III

A product obtained by coupling oestradiol and cytochrome c peroxidase was taken up in the following buffers:

(a) 0.36 M HEPES, 2% sucrose, 6% mannitol, 0.01 M EDTA and 0.01 M FeSO$_4$ (pH 7.4)

(b) As (a), but omitting FeSO$_4$.

The solutions were freeze-dried and kept at 37° C.

The peroxidase content was 270 ng/ml.

After 16 weeks, the enzyme activity of product (a) was practically unchanged, and the behaviour in an enzyme immunotest was the same as that of the original enzyme conjugate, while the enzyme activity of product (b) had fallen to less than 50% of the original activity.

EXAMPLE IV

A product obtained by coupling oestriol and horse radish peroxidase was dissolved in the following media:

(a) 0.01 M HEPES, 0.01 M EDTA, 2% sucrose and 0.01 M Al$_2$(SO$_4$)$_3$.

(b) As (a), but omitting Al$_2$(SO$_4$)$_3$.

The peroxidase content of both solutions was 180 ng/ml.

Both solutions were freeze-dried in droplet form as described in example II and were then kept at 37° C.

After 11 weeks, the peroxidase activity of product (a) was unchanged, while the enzyme activity of product (b) had already disappeared after a few days.

EXAMPLE V

In a way corresponding to that described in example III, a product obtained by coupling human placental lactogen (HPL) and horse radish peroxidase (HRP-RZ 0.6) was dissolved, freeze-dried and stored.

Product (a): after 22 weeks, 94% enzyme activity.

Product (b): after 22 weeks, no enzyme activity.

Analogous results were obtained with a product obtained by coupling anti-hepatitis B antibodies and horse radish peroxidase, but replacing the FeSO$_4$ in solution (a) my MgSO$_4$ as stabilizer, and with a product obtained by coupling sheep antibodies against human immunoglobulin and cytochrome c peroxidase, but using ZnCl$_2$ as the stabilizer in solution (a).

What is claimed is:

1. A reagent for the determination of a component of the antigen-antibody reaction comprising:
   (1) one member of the group consisting of an antigen and an antibody capable of reacting with said antigen; and
   (2) the other member of (1) covalently linked to the peroxidase present in a freeze-dried composition comprising:
      (a) a peroxidase; and
      (b) one or more polyvalent metal ions selected from the group consisting of Mg, Ca, Sc, Ti, V, Cr, Mn, Fe, Co, Ni, Cu, Zn, Ga, and Al present in an amount of at least 0.0001 M.

2. A reagent as recited in claim 1 wherein the polyvalent ion is part of an iron salt.

3. A reagent as recited in claim 1 wherein the polyvalent ion is part of an aluminum salt.

4. A reagent as recited in claim 1 wherein the peroxidase is horseradish peroxidase.

5. A reagent for use in enzyme immunoassay tests for the determination of a hapten being a protein-free substance that is not capable of stimulating antibody formation but which reacts with specific antibodies, comprising:
   (1) the coupling product of said hapten and a peroxidase present in a freeze-dried composition comprising:
      (a) a peroxidase; and
      (b) one or more polyvalent metal ions selected from the group consisting of Mg, Ca, Sc, Ti, V, Cr, Mn, Fe, Co, Ni, Cu, Zn, Ga, and Al present in an amount of at least 0.0001 M; and
   (2) A binding protein capable of reacting to bind said hapten and said hapten-peroxidase containing composition coupling product.

6. A reagent for the determination of a component of an antigen-antibody reaction by enzyme immunoassay comprising:
   (1) one of the members of the group consisting of an antigen and an antibody capable of reacting with said antigen, said member coupled to a carrier and
   (2) a substance having the same immunochemical properties as the member in (1) covalently linked to the peroxidase present in a freeze-dried composition comprising:
      (a) a peroxidase; and
      (b) at least one polyvalent metal ion selected from the group consisting of Mg, Ca, Sc, Ti, V, Cr, Mn, Fe, Co, Ni, Cn, Zn, Ga, and Al present in an amount of at least 0.0001 M.

* * * * *